United States Patent
Sheetz et al.

(10) Patent No.: US 8,476,065 B2
(45) Date of Patent: Jul. 2, 2013

(54) DEVICE FOR MEASURING NANOMETER LEVEL PATTERN-DEPENDENT BINDING REACTIONS

(75) Inventors: Michael P. Sheetz, New York, NY (US); Samuel J. Wind, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 996 days.

(21) Appl. No.: 11/404,716

(22) Filed: Apr. 13, 2006

(65) Prior Publication Data

US 2007/0048790 A1    Mar. 1, 2007

Related U.S. Application Data

(63) Continuation of application No. PCT/US2004/034987, filed on Oct. 15, 2004.

(60) Provisional application No. 60/511,799, filed on Oct. 15, 2003.

(51) Int. Cl.
*C12M 3/00* (2006.01)

(52) U.S. Cl.
USPC ............ 435/287.9; 422/50; 422/68.1; 435/4; 435/283.1; 435/288.3; 435/288.4; 435/975; 977/700; 977/701; 977/702; 977/705; 977/789; 977/793

(58) Field of Classification Search
USPC ........... 422/50, 61, 68.1; 435/4, 283.1, 287.9, 435/288.3, 288.4, 975; 977/700, 701, 702, 977/705, 789, 793
See application file for complete search history.

(56) References Cited

U.S. PATENT DOCUMENTS

| | | | | |
|---|---|---|---|---|
| 5,565,186 A | * | 10/1996 | Prusiner et al. | 800/3 |
| 6,225,047 B1 | * | 5/2001 | Hutchens et al. | 435/5 |
| 6,258,841 B1 | * | 7/2001 | Uckun et al. | 514/461 |
| 6,287,765 B1 | | 9/2001 | Cubicciotti | |
| 6,329,209 B1 | * | 12/2001 | Wagner et al. | 506/13 |
| 6,406,921 B1 | | 6/2002 | Wagner et al. | |
| 6,436,933 B1 | * | 8/2002 | Rideout et al. | 514/235.8 |
| 6,685,841 B2 | * | 2/2004 | Lopez et al. | 210/767 |
| 6,828,110 B2 | * | 12/2004 | Lee et al. | 435/7.1 |

(Continued)

FOREIGN PATENT DOCUMENTS

WO    WO-95/20601 A1    8/1995

OTHER PUBLICATIONS

PCT Application No. PCT/US04/34987, International Search Report mailed Jul. 20, 2005, 4 pgs.

(Continued)

*Primary Examiner* — Melanie Y Brown
*Assistant Examiner* — Erik B Crawford
(74) *Attorney, Agent, or Firm* — Schwegman Lundberg Woessner P.A.

(57) ABSTRACT

The present invention is directed to a device comprising (a) a substrate having a surface and (b) an ordered array of posts over the surface, wherein the posts are capable of binding a protein or small molecule ligand, and wherein the pitch between adjacent posts is less than about 100 nm. The invention is also directed to methods for identifying the presence of an analyte in a fluid and to methods for measuring relative binding specificity or affinity between an analyte in a fluid and the posts, using the device of the present invention.

18 Claims, 16 Drawing Sheets

U.S. PATENT DOCUMENTS

| | | | |
|---|---|---|---|
| 6,875,274 | B2 | 4/2005 | Wong et al. |
| 7,183,050 | B2 | 2/2007 | Krull |
| 2003/0134267 | A1* | 7/2003 | Kang et al. .................. 435/4 |
| 2003/0185985 | A1 | 10/2003 | Bronikowski et al. |
| 2004/0219526 | A1* | 11/2004 | Reddy et al. ................. 435/6 |
| 2007/0264675 | A1* | 11/2007 | Toner et al. .............. 435/7.23 |
| 2008/0003615 | A1 | 1/2008 | Sheetz et al. |

OTHER PUBLICATIONS

PCT Application No. PCT/US04/34987, Written Opinion mailed Jul. 30, 2005, 6 pgs.

Amos, L. A., "Brain Dynein Crossbridges Microtubules Into Bundles", *Journal of Cell Science*, 93(1), (1989), 19-28.

Broers, A. N., "Resolution Limits for Electron-Beam Lithography", *IBM Journal of Research and Development*, 32(4), (1988), 502-513.

Calderwood, D. A., et al., "Talin Forges the Links Between Integrins and Actin", *Nature Cell Biology*, 5, (2003), 694-697.

Cherniavskaya, O., et al., "Fabrication and Surface Chemistry of Nanoscale Bioarrays Designed for the Study of Cytoskeletal Protein Binding Interactions and Their Effect on Cell Motility", *Journal of Vacuum Science & Technology B*, 23(6), (2005), 2972-2978.

Coussen, F., et al., "Trimers of the Fibronectin Cell Adhesion Domain Localize to Actin Filament Bundles and Undergo Rearward Translocation", *Journal of Cell Science*, 115(12), (2002), 2581-2590.

Dhermy, D. D., et al., "The Spectrin Super-Family", (1991), *Biology of the Cell*, 71(3), (1991), 249-254.

Djinovic-Carugo, K., et al., "The Spectrin Repeat: A Structural Platform for Cytoskeletal Protein Assemblies", *FEBS Letters*, 513(1), (2002), 119-123.

Dobisz, E. A., et al., "Effects of Molecular Properties on Nanolithography in Polymethyl Methacrylate", *Journal of Vacuum Science & Technology B*, 18(1), (2000), 107-111.

Gee, M. A., et al., "An Extended Microtubule-Binding Structure Within the Dynein Motor Domain", *Nature*, 390, (1997), 636-639.

Gelles, J., et al., "Tracking Kinesin-Driven Movements With Nanometre-Scale Precision", *Nature* 331(6155) 1998, 450-453.

Goldmann, W. H., et al., "Vinculin, Talin and Focal Adhesions", *Journal of Muscle Research and Cell Motility*, 17, (1996), 1-5.

Guillorn, M. A., et al., "Fabrication of Dissimilar Metal Electrodes With Nanometer Interelectrode Distance for Molecular Electronic Device Characterization", *Journal of Vacuum Science & Technology B*, 18(3), (2000), 1177-1181.

Isaacson, M., et al., "In situ Vaporization of Very Low Molecular Weight Resists Using 1/2 nm Diameter Electron Beams", *Journal of Vacuum Science & Technology*, 19(4), (1981),1117-1120.

Jiang, G., et al., "Two-Piconewton Slip Bond Between Fibronectin and the Cytoskelton Depends on Talin", *Nature*, 424(6946), (2003), 334-337.

Langheinrich, W., et al., "Fabrication of Metallic Region in the 10nm Region Using an Inorganic Electron Beam Resist", *Japanese. Journal of Applied Physics*, 32, (1993), 6218-6223.

Marrian, C. R., et al., "Nanofabrication", *Journal of Vacuum Science & Technology A*, 21(5), (2003), S207-S215.

Mazumdar, M., et al., "In vitro Motility from Recombinant Dynein Heavy Chain", *Proc. Natl. Acad. Sci. USA*, 93(13), 1996, 6552-6556.

Namatsu, H., et al., "Influence of Edge Roughness in Resist Patterns on Etched Patterns", *Journal of Vacuum Science & Technology B*, 16(6), (1998), 3315-3321.

Namatsu, H., et al., "Three-Dimensional Siloxane Resist for the Formation of Nanopatterns With Minium Linewidth Fluctuations", *Journal of Vacuum Science & Technology B*, 16(1), (1998), 69-76.

Rooks, M. J., et al., "Application of 4-methyl-1-acetoxycalix[6]arene Resist to Complementary Metal-Oxide-Semiconductor Gate Processing", *Journal of Vacuum Science & Technology B*, 17(6), (1999),3394-3397.

Rooks, M. J., et al., "Low Stress Development of Poly(methylmethacrylate) for High Aspect Ratio Structures", *Journal of Vacuum Science & Technology B*, 20(6), (2002), 2937-2941.

Sakakibara, H., et al., "Inner-Arm Dynein c of *Chlamydomonas flagella* is a Single-Headed Processive Motor", *Nature*, 400, (1999), 586-590.

Siew, Y. K., et al., "Thermal Curing of Hydrogen Silsesquioxane", *Journal of The Electrochemical Society*, 147(1), (2000), 335-339.

Tang, J., et al., "Chemically Responsive Molecular Transistors Fabricated by Self-Aligned Lithography and Chemical Self-Assembly", *Journal of Vacuum Science & Technology B*, 24(6), (2006), 3227-3229.

Ulman, A., "Formation and Structure of Self-Assembled Monolayers", *Chemical Reviews*, 96(4), (1996),1533-1554.

Wang, Z., et al., "Single Cytoplasmic Dynein Molecular Movements: Characterization and Comparison With Kinesin", *Biophysical Journal*, 69, (1995), 2011-2023.

Whitesides, G. M., et al., "Molecular Self-Assembly and Nanochemistry: A Chemical Strategy for the Synthesis of Nanoparticles", *Science*, 254(5036), (1991), 1312-1319.

Wind, S. J., et al., "Transistor Structures for the Study of Scaling in Carbon Nanotubes", *Journal of Vacuum Science & Technology B*, 21(6), (2003), 2856-2859.

Winkler, J., et al., "Energy-Filtered Electron Microscopy Reveals That Talin is a Highly Flexible Protein Composed of a Series of Globular Domains", *European. Journal of Biochemistry*, 243(1-2), (1997),430-436.

Yasin, S., et al., "Fabrication of <5 nm Width Lines in Poly(methylmethacrylate) Resist Using a Water: Isopropyl Alcohol Developer and Ultrasonically-Assisted Development", *Applied Physics Letters*,78(18), (2001), 2760-2762.

Yasin, S., et al., "Nanolithography Using Ultrasonically Assisted Development of Calixarene Negative Electron Beam Resist", *Journal of Vacuum Science and Technology B*, 19(1), (2001), 311-313.

"U.S. Appl. No. 11/652,809, Non Final Office Action mailed on Mar. 23, 2009", 10 pgs.

Hoyer, P., "Formation of a Titanium Dioxide Nanotube Array", *Langmuir*, 12, (1996), 1411-1413.

"U.S. Appl. No. 11/652,809, Response filed Sep. 15, 2009 to Non Final Office Action mailed Mar. 23, 2009", 8 pgs.

"U.S. Appl. No. 11/652,809, Final Office Action mailed Jan. 7, 2010", 13 pgs.

"U.S. Appl. No. 11/652,809, Advisory Action mailed Apr. 29, 2010", 3 pgs.

"U.S. Appl. No. 11/652,809, Response filed Apr. 6, 2010 to Final Office Action mailed Jan. 7, 2010", 15 pgs.

* cited by examiner

PMMA

Direct patterning on SAMS

US 8,476,065 B2

DEVICE FOR MEASURING NANOMETER LEVEL PATTERN-DEPENDENT BINDING REACTIONS

This application is a continuation of International Application Serial No. PCT/US2004/034987, filed Oct. 15, 2004, which claims the benefit of provisional application U.S. Ser. No. 60/511,799, filed Oct. 15, 2003, which are hereby incorporated by reference into the subject application in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

Copyright Statement: copyright in the text and graphic materials contained in this disclosure is owned by Columbia University of New York. The materials contained in this disclosure may be used, downloaded, reproduced or reprinted, provided that this copyright notice appears in all copies and provided that such use, download, reproduction or reprint is for noncommercial or personal use only. The materials contained in this disclosure may not be modified in any way.

FIELD OF THE INVENTION

This invention is directed to the field of nanometer array devices, detection methods, and analytical methods.

BACKGROUND OF THE INVENTION

Many proteins have been studied extensively at the single molecule level. However, in the cell those proteins form into larger complexes or modules wherein the spacing of components on a nanometer scale is critical. New technologies in patterning and stamping now enable us to systematically measure the dependence of interactions on nanometer level patterns and to then exploit that spatial dependence in sensing and nanofabrication of materials through directed self-assembly. As an example, the signals from extracellular matrices affect normal and cancerous cell growth and there is evidence that the spacing of the matrix molecules makes a critical difference in that signal (Jiang, G. et al. (2003) *Nature*, 424: 334-37). These mechanisms must be studied at a scale that matches the size and/or spacing of features of specific protein or subcellular protein complexes, which are generally at the nanometer level.

There is a great need to measure the binding of complex protein assemblies with spatially ordered ligands. Thus, there is a great need for a device that tests the binding of an analyte to specific spatial arrays of ligands.

SUMMARY OF THE INVENTION

The present invention is directed to a device comprising (a) a substrate having a surface and (b) an ordered array of posts over the surface, wherein the posts are capable of binding a protein or small molecule ligand, and wherein the pitch between adjacent posts is less than about 100 nm.

The invention is also directed to methods for identifying the presence of an analyte that binds to the arrayed ligand from a fluid comprising (a) providing a device comprising a substrate having a surface, the surface comprising an ordered array of posts over the surface, wherein the pitch between adjacent posts is less than about 100 nm, wherein each post is coated with ligand, (b) contacting the surface of the device with a fluid sample, and (c) determining whether or not an analyte in the fluid sample interacts or binds to a ligand-coated post, thereby identifying the presence of the analyte in the fluid sample. The method can also include the step of purifying the analyte.

The present invention is further directed to methods for measuring relative binding specificity or affinity between an analyte and a ligand simultaneously affixed to at least two posts, comprising (a) providing a device comprising a substrate having a surface, wherein the surface comprises an ordered array of posts over the surface, wherein the pitch between adjacent posts is less than about 100 nm, (b) contacting the surface of the device with a fluid comprising an analyte, (c) determining whether or not an analyte in the fluid sample interacts or binds to the ligand, and (d) determining the binding specificity or affinity between the analyte and the ligand.

The invention is also directed to a method for crystallizing a protein comprising (a) providing a device comprising a substrate having a surface, wherein the surface comprises an ordered array of posts over the surface, wherein the pitch between adjacent posts is less than about 100 nm, wherein each post is capable of binding a protein, and (b) contacting the surface of the device with protein to be crystallized, wherein at least one post functions as a seed crystal or nucleus for crystallization, thereby crystallizing the protein.

The invention is directed to making a device according to the present invention comprising (a) designing an array pattern, (b) writing the array pattern onto a substrate, (c) forming a post on the substrate, and optionally (d) shrinking the post, thereby making the device.

The invention is also directed to a kit for determining the presence or absence of an analyte in a sample, or for determining a subject's risk for developing a disease, or for monitoring the status of a disease in a subject that comprises a device that specifically binds to an analyte in an amount effective to detect the analyte in a sample. The kit contains a device comprising (a) a substrate having a surface and (b) an ordered array of posts over the surface, wherein the posts are capable of binding a ligand and wherein the pitch between adjacent posts is less than about 100 nm. Further, the interaction between the posts and the analyte is detectable. The posts of the kit, in one embodiment, include one or more ligands attached thereto. The kit can include one or more reagents for detecting amounts of one or more analytes bound to the device.

The invention is also directed to a method for detecting a protein isomer in a mixture, the method comprising (a) providing a device comprising a substrate having a surface; the surface comprising an ordered array of posts over the surface, wherein the pitch between adjacent posts is less than about 100 nm, wherein each post is coated with ligand; (b) contacting the surface of the device with a mixture; and (c) determining whether or not a protein isomer in the mixture interacts or binds to a ligand-coated post, thereby detecting the protein isomer in the mixture.

The invention is directed to a method for detecting a microorganism in a fluid sample, the method comprising (a) providing a device comprising a substrate having a surface; the surface comprising an ordered array of posts over the surface, wherein the pitch between adjacent posts is less than about 100 nm, wherein each post is coated with ligand; (b) contacting the surface of the device with a fluid sample; and (c) determining whether or not a microorganism in the fluid sample interacts or binds to a ligand-coated post, thereby detecting the microorganism in the fluid sample.

DETAILED DESCRIPTION OF THE INVENTION

Figure 1:
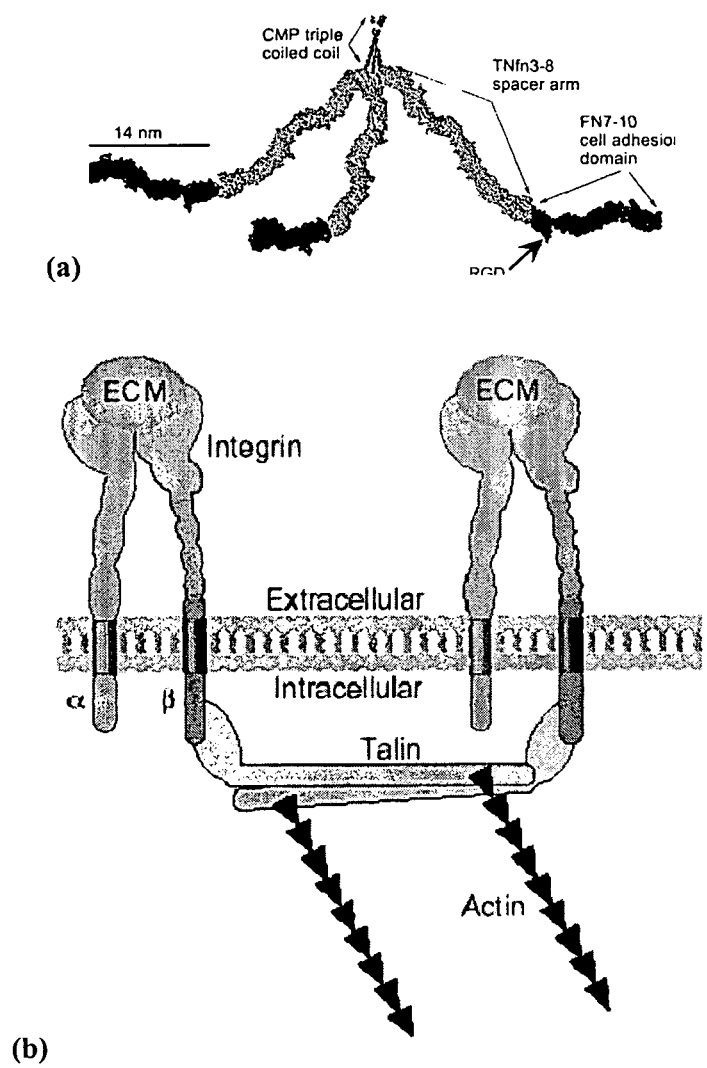
FIG. 1 depicts fibronectin and a slip bond formed between a single trimer of fibronectin and a cellular cytoskeleton.

The present invention enables the formation of protein arrays on the scale of nanometers as in a cell and the application of this technology to measure and exploit the spatial dependence of interactions in biological and nanofabrication areas. There is a critical need to control the spatial parameter in molecular interactions in a defined way.

The invention provides a device that facilitates binding of an analyte to a set of posts having a spacing that facilitates the binding. Binding to a single post is dependent upon the chemistry and steric nature of the analyte and the protein attached to the post.

The present invention is directed to a device comprising (a) a substrate having a surface and (b) an ordered array of posts over the surface, wherein the posts are capable of binding a protein or small molecule ligand, and wherein the pitch between adjacent posts is less than about 100 nm.

In one embodiment, the device comprises a gradient of pitch values. In one embodiment, the gradient of pitch values is from about 5 nm to about 100 nm.

In another embodiment, each post is less than about 20 nm in diameter. In other embodiments, each post is less than about 10 nm in diameter, less than about 5 nm in diameter, less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, or a combination thereof.

In another embodiment, each post has affixed thereto exactly one protein molecule. In another embodiment, each post displays more than one protein molecule. In another embodiment, the protein molecule comprises at least a portion of a full-length dynein heavy chain, tubulin, kinesin, myosin, at least a portion of a cytoplasmic domain of an integrin, actin, extracellular matrix ligand fragments, fibronectin, collagen, laminin, DNA solenoids, DNA, histone-DNA complexes, RNA, RNA-protein complexes, bacterial coat proteins, antibodies, lectins, or avidin. In one embodiment, the protein molecule comprises a full-length dynein heavy chain, the dynein motor domain, or the N-terminal half of the dynein motor domain.

In one embodiment, the pitch is less than about 50 nm. In other embodiments, the pitch is less than about 40 nm, less than about 35 nm, less than about 30 nm, less than about 25 nm, less than about 20 nm, less than about 15 nm, less than about 10 nm, and in another embodiment, less than about 5 nm.

In another embodiment, the pitch is homogenous. In another embodiment, the pitch is not homogeneous.

In one embodiment, the device comprises an ordered array of pairs of posts, wherein the pitch between each member in the pair of posts is less than about 50 nm.

The invention is also directed to methods for identifying the presence of an analyte that binds to the arrayed ligand from a fluid comprising (a) providing a device comprising a substrate having a surface, the surface comprising an ordered array of posts over the surface, wherein the pitch between adjacent posts is less than about 100 nm, wherein each post is coated with ligand, (b) contacting the surface of the device with a fluid sample, and (c) determining whether or not an analyte in the fluid sample interacts or binds to a ligand-coated post, thereby identifying the presence of the analyte in the fluid sample. The method can also include the step of purifying the analyte.

In one embodiment, the determining step of the method comprises use of optical, electrical, or mechanical means, or a combination thereof. In one embodiment, the determining step comprises use of total internal reflection fluorescence (TIRF) microscopy, ellipsometry, or phase microscopy, atomic force microscopy (AFM), fluorescence resonance energy transfer (FRET) microscopy, fluorescence microscopy, two-photon microscopy, electrical conduction, or a combination thereof. In another embodiment, the determining step comprises use of TIRF microscopy.

In one embodiment, the device used in the method comprises a gradient of pitch values. In one embodiment, the gradient of pitch values is from about 5 nm to about 100 nm.

In another embodiment, each post is less than about 20 nm in diameter. In other embodiments, each post is less than about 10 nm in diameter, less than about 5 nm in diameter, less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, or a combination thereof.

In another embodiment, each post displays exactly one protein molecule. In another embodiment, each post displays more than one protein molecule. In another embodiment, the protein molecule comprises at least a portion of a full-length dynein heavy chain, tubulin, kinesin, myosin, at least a portion of a cytoplasmic domain of an integrin, actin, extracellular matrix ligand fragments, fibronectin, collagen, laminin, DNA solenoids, DNA, histone-DNA complexes, RNA, RNA-protein complexes, bacterial coat proteins, antibodies, lectins, or avidin. In one embodiment, the protein molecule comprises a full-length dynein heavy chain, the dynein motor domain, or the N-terminal half of the dynein motor domain.

In one embodiment, the pitch is less than about 50 nm. In other embodiments, the pitch is less than about 40 nm, less than about 35 nm, less than about 30 nm, less than about 25 nm, less than about 20 nm, less than about 15 nm, less than about 10 nm, and in another embodiment, less than about 5 nm.

In another embodiment, the pitch is homogenous. In another embodiment, the pitch is not homogenous.

In one embodiment, the device used in the method comprises an ordered array of pairs of posts, wherein the pitch between each member in the pair of posts is less than about 50 nm.

The present invention is further directed to methods for measuring relative binding specificity or affinity between an analyte and a ligand simultaneously affixed to at least two posts, comprising (a) providing a device comprising a substrate having a surface, wherein the surface comprises an ordered array of posts over the surface, wherein the pitch between adjacent posts is less than about 100 nm, (b) contacting the surface of the device with a fluid comprising an analyte, (c) determining whether or not an analyte in the fluid sample interacts or binds to the ligand, and (d) determining the binding specificity or affinity between the analyte and the ligand.

In one embodiment, the relative binding specificity or affinity is a function of pitch.

In one embodiment, the determining step of the method comprises use of optical, electrical, or mechanical means, or a combination thereof. In one embodiment, the determining comprises use of TIRF microscopy, ellipsometry, or phase microscopy, AFM, FRET microscopy, fluorescence microscopy, two-photon microscopy, electrical conduction, or a combination thereof. In another embodiment, the determining comprises use of TIRF microscopy.

In one embodiment, the device used in the method comprises a gradient of pitch values. In one embodiment, the gradient of pitch values is from about 5 nm to about 100 nm.

In another embodiment, each post is less than about 20 nm in diameter. In one embodiment, each post is less than about 10 nm in diameter, less than about 5 nm in diameter, less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, or a combination thereof.

In another embodiment, each post displays exactly one protein molecule. In another embodiment, each post displays more than one protein molecule. In another embodiment, the protein molecule comprises at least a portion of a full-length dynein heavy chain, tubulin, kinesin, myosin, at least a portion of a cytoplasmic domain of an integrin, actin, extracellular matrix ligand fragments, fibronectin, collagen, laminin, DNA solenoids, DNA, histone-DNA complexes, RNA, RNA-protein complexes, bacterial coat proteins, antibodies, lectins, or avidin. In one embodiment, the protein molecule comprises a full-length dynein heavy chain, the dynein motor domain, or the N-terminal half of the dynein motor domain.

In one embodiment, the pitch is less than about 50 nm. In one embodiment, the pitch is less than about 40 nm, less than about 35 nm, less than about 30 nm, less than about 25 nm, less than about 20 nm, less than about 15 nm, less than about 10 nm, and in another embodiment, less than about 5 nm.

In another embodiment, the pitch is homogenous. In another embodiment, the pitch is not homogenous.

In one embodiment, the device used in the method comprises an ordered array of pairs of posts, wherein the pitch between each member in the pair of posts is less than about 50 nm.

The invention is also directed to a method for crystallizing a protein comprising (a) providing a device comprising a substrate having a surface, wherein the surface comprises an ordered array of posts over the surface, wherein the pitch between adjacent posts is less than about 100 nm, and is identical throughout the array, and wherein each post is capable of binding a protein, and (b) contacting the surface of the device with protein to be crystallized, wherein at least one post functions as a seed crystal or nucleus for crystallization, thereby crystallizing the protein.

In one embodiment, the device used in the method comprises a gradient of pitch values. In one embodiment, the gradient of pitch values is from about 5 nm to about 100 nm.

In another embodiment, each post is less than about 5 nm in diameter. In one embodiment, each post is less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, and or a combination thereof.

In another embodiment, each post displays exactly one protein molecule. In another embodiment, the protein molecule comprises at least a portion of a full-length dynein heavy chain, tubulin, kinesin, myosin, at least a portion of a cytoplasmic domain of an integrin, actin, extracellular matrix ligand fragments, fibronectin, collagen, laminin, DNA solenoids, DNA, histone-DNA complexes, RNA, RNA-protein complexes, bacterial coat proteins, antibodies, lectins, or avidin. In one embodiment, the protein molecule comprises a full-length dynein heavy chain, the dynein motor domain, or the N-terminal half of the dynein motor domain.

In one embodiment, the pitch is less than about 20 nm. In one embodiment, the pitch is less than about 15 nm, less than about 10 nm, and in another embodiment, less than about 5 nm.

In another embodiment, the pitch is homogenous.

The invention is directed to making a device according to the present invention comprising (a) designing an array pattern, (b) writing the array pattern onto a substrate, (c) forming a post on the substrate, and optionally (d) shrinking the post, thereby making the device.

In one embodiment, designing the array pattern comprises using a computer-aided design or an algorithmic design system. In another embodiment, the algorithmic design system allows for the systematic variation of post configuration and spacing.

In another embodiment, writing the array pattern comprises using a high resolution electron beam lithography system. In one embodiment, writing the array pattern comprises patterning a mask.

In one embodiment, the substrate is coated with a resist. In one embodiment, the resist is a positive resist. In another embodiment, the resist is a negative resist.

In another embodiment, forming the post comprises a technique selected from the group consisting of liftoff, electroplating, reactive ion etching, ion milling, controlled wet etching, or a combination thereof.

In one embodiment, the method of making the device further comprises forming microfluidic channels. In one embodiment, the method further comprises binding a ligand to a post on the device.

The invention is also directed to a kit for determining the presence or absence of an analyte in a sample or for determining a subject's risk for developing a disease or for monitoring the status of a disease in a subject that comprises a device that specifically binds to an analyte in an amount effective to detect the analyte in the sample. The kit contains a device comprising (a) a substrate having a surface and (b) an ordered array of posts over the surface, wherein the posts are capable of binding a ligand and wherein the pitch between adjacent posts comprises less than about 100 nm. Further, the interaction between the device and the analyte is detectable. The kit can include one or more reagents for detecting amounts of one or more analytes bound to the device.

In one embodiment, the sample is a blood sample or a serum sample.

In another embodiment, the kit further comprises one or more reagents for detecting amounts of the one or more analytes bound to the device.

In one embodiment, the analyte is labeled with a detectable marker. In one embodiment, the detectable marker is selected from the group consisting of a fluorescent marker, a radioactive marker, an enzymatic marker, a colorimetric marker, a chemiluminescent marker or a combination thereof.

The invention is further directed to a method for detecting a protein isomer in a mixture, the method comprising (a) providing a device comprising a substrate having a surface; the surface comprising an ordered array of posts over the surface, wherein the pitch between adjacent posts is less than about 100 nm, wherein each post is coated with ligand; (b) contacting the surface of the device with a mixture; and (c) determining whether or not a protein isomer in the mixture interacts or binds to a ligand-coated post, thereby detecting the protein isomer in the mixture.

In one embodiment, the device used in the method comprises a gradient of pitch values. In one embodiment, the gradient of pitch values is from about 5 nm to about 100 nm.

In another embodiment, each post is less than about 5 nm in diameter. In one embodiment, each post is less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, and or a combination thereof.

The invention is directed to a method for detecting a microorganism in a fluid sample, the method comprising (a) providing a device comprising a substrate having a surface; the surface comprising an ordered array of posts over the surface, wherein the pitch between adjacent posts is less than about 100 nm, wherein each post is coated with ligand; (b) contacting the surface of the device with a fluid sample; and (c) determining whether or not a microorganism in the fluid sample interacts or binds to a ligand-coated post, thereby detecting the microorganism in the fluid sample.

In one embodiment, the device used in the method comprises a gradient of pitch values. In one embodiment, the gradient of pitch values is from about 5 nm to about 100 nm.

In another embodiment, each post is less than about 5 nm in diameter. In one embodiment, each post is less than about 3 nm in diameter, and in another embodiment, less than about 2 nm in diameter.

In one embodiment, each post independently comprises a material selected from the group consisting of metal, semiconductor, organic insulator, inorganic insulator, biocompatible material, or a combination thereof. In one embodiment, each post independently comprises a material selected from gold, nickel, polyethyleneglycol, and or a combination thereof.

The term "post" is used herein to mean a support rising vertically from the surface of the substrate.

The term "surface" is used herein to mean the outer part of a substrate.

The term "pitch" is used herein to mean the distance between center points of adjacent posts.

The term "gradient" is used herein to mean a gradual change.

The term "biocompatible" is used herein to mean being compatible with living tissue by virtue of a lack of toxicity or ability to cause immunological response.

The term "TIRF" is used herein to mean total internal reflection fluorescence.

The term "FRET" is used herein to mean fluorescence resonance energy transfer.

The term "AFM" is used herein to mean atomic force microscopy.

The term "PMMA" is used herein to mean poly(methyl) methacrylate.

The term "resist" is used herein to mean a radiation sensitive layer.

The term "CAD" is used herein to mean computer aided design.

The term "unit cell" as used herein refers to a set of posts having a specific geometric configuration, which can include a pair of posts separated by a given spacing, which is then varied; or a small number of posts separated by a given spacing with fixed angles between them, so that they may be arranged as, for example, squares, rectangles, or general trapezoids.

The term "AAA" is used herein to mean ATPases associated with cellular activity.

The term "HC" is used herein to mean heavy chain.

The term "IPA" is used herein to mean isopropanol.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

In one embodiment of the invention, the subject is a mammal. The mammal can be a human or a primate. The subject can be a human patient, or an animal that exhibits symptoms of a human immune disease and is therefore an animal model of a human disease, such as a murine transgenic disease model or a primate disease model or a model of human disease established in a SCID mouse reconstituted with the human immune system. The mammal can be, but is not limited to, a human, a primate, a rat, a dog, a cat, a swine. In another aspect of the invention, the subject is a murine subject, a bovine subject, a primate subject, an equine subject, a swine subject, or a canine subject.

Nanoarray Device and Uses Thereof

In one embodiment of the invention is provided a device comprising (a) a substrate having a surface and (b) an ordered array of posts over the surface, wherein the posts are capable of binding a ligand, and wherein the pitch between adjacent posts is less than about 100 nm. The device according to the present invention is a flexible device that provides many new capabilities for measuring not only the spatial dependence of binding to one ligand, but also the spatial dependence of binding to several different ligands that are patterned on the surface. Using high throughput techniques, including multiple stamping techniques, several different chemicals could be patterned on a surface; for example, gold dots followed by nickel dots can create a pattern for binding sulfhydryl and poly-histidine tags, respectively. Stamping techniques include nanoimprint lithography and contact printing.

In another embodiment of the present invention is provided a method to rapidly measure highly specific interactions that depend upon the molecular level spacing of components in large complexes. By changing the distance between 2-5 nm posts on the nanometer scale, it is possible to create spatial arrays of ligands that match the spacing and distribution of binding sites in a binding complex. Binding constants can be measured directly using a microfluidics flow system and either TIRF microscopy or ellipsometric measurements to monitor the rates of binding and release of the material at known concentrations.

In a typical measurement, an array of 2-5 nm posts are created on the stamp. The stamp is then used to create a pattern of dots on a small area (light microscope resolution limits the minimum size for reliable measurements to 2-5 $\mu m^2$) of a glass coverslip. Tens to hundreds of different patterns are stamped on adjacent regions of the coverslip to fill the 10,000 $\mu m^2$ viewing area of the microscope objective (typically a 60×, 1.45 n.a. objective capable of through objective TIRF). Once stamped with the designated patterns, the stamped coverslip is assembled with a microfluidics channel and the ligands are bound to the appropriate dots on the array. After washing and blocking the rest of the surface to prevent non-specific interactions, the binding molecules tagged with an appropriate fluorophore are added through the flow channel, incubated to allow binding, and washed out to measure release. Continuous monitoring by TIRF microscopy enables the rates of binding and release to be measured simultaneously for all different ligand configurations. Regions with the optimal spacing are then correlated with the structure of the binding complex, where known.

In diagnostic applications, configurations are selected that give the greatest discrimination in binding between different complexes or bacterial species. The rate-limiting step in these measurements may be the off rate, since binding affinities are expected to be very high for the multiple sites. For some applications where multiple measurements are to be made, the device is washed with mild denaturants to remove the bound complexes.

Stamping enables the mass production of the arrays and the TIRF microscopy is automated to perform the measurements on a series of samples. Standard arrays are constructed for general research applications.

Molecular specificity with randomly oriented ligands on surfaces confers a range of binding affinities whereas this technique should provide critical spatial ordering on the molecular scale that would show a high degree of specificity. Many cellular functions rely upon this spatial order to confer specificity and there are an increasing number of nanodevices that will have a similar spatial order on the nanometer level. Measuring spatial dependent binding is critical for defining both cellular and artificial complexes.

The device according to the present invention utilizes the spatial dependence of binding to provide further specificity of binding. Several different spacings are placed on the surface in adjacent areas in the microscope field so that relative binding specificity is measured simultaneously. A microfluidics flow channel over the device enables measurements to be made with as little as 1 microliter of material. The amount of binding is determined by total internal reflection fluorescence microscopy and on and off rates from regions with different spacings enables the proper spacing to be determined. For larger scale purifications and analyses, the optimal spacing is used to create an area large enough for a standard ellipsometry measurement, thus enabling purification and other types of analyses that need larger amounts of material, and expanding the range of uses of the spatial binding techniques.

Specificity of binding is much greater with proper spacing of multiple sites because physical chemical calculations indicate that the binding affinity increases to at least the product of the affinity constants. In addition, other spacings on adjacent regions of the same device provide controls for non-specific interactions. Because the volume of material needed for a measurement is very small (1 microliter), it is possible to test extremely small samples.

In Vitro Motor and Motility Analysis

Motor proteins such as kinesin and cytoplasmic dynein have been studied extensively at the single molecule level. However, there are many questions about the structure of these proteins and the mechanism of motility that cannot be addressed without being able to alter the array of proteins that the motors move upon. For dynein, there are also questions about the in vitro synthesized motor domain function that can be addressed by arraying it on the surface. In terms of the microtubules, different microtubule arrays have been formed but there is no current mechanism to systematically alter the array of tubulin subunits and then to assay for binding and/or motility. Using the device and methods of the present invention, the effect of tubulin dimer spacing on motor binding are determined using GFP-tubulin that is bound to a specific array of anti-GFP antibodies. A parallel analysis of myosin binding to arrayed actin monomers is also performed. By engineering tubulin dimers, dimers that can be oriented on a stamped array are developed. The ordered arrays provide one means of carrying out an in vitro motility assay and determining the effect of array characteristics on motor function. This is an area of motor function that has not been addressed because it has not been possible with earlier technologies.

While much is known of the molecular mechanism of other classes of motor proteins, insight into the mechanism of action of the dyneins remains limited because of their large size. The dyneins are a family of microtubule based motor proteins responsible for ciliary and flagellar motility, and play diverse roles in cell division, organelle transport, and cell movement. The dynein motor domain is unrelated to that of other cellular motors, but is a relatively divergent member of the class of ATPases associated with cellular activity. Each dynein heavy chain subunit contains six AAA modules arrayed in a ring, from which two projections emerge. One is referred to as the stalk, and binds microtubules to its distal tip about 10 nm from the edge of the AAA ring. How ATP hydrolysis by the AAA units is converted into movement is poorly understood. Kinesin is much better understood as a motor. The microtubule binding characteristics of kinesin have been extensively studied and provide a nice comparison for the dynein binding characteristics.

Ordered nanoarrays provide an improved and in many cases unique tool to address a variety of important questions regarding dynein mechanochemistry. Cytoplasmic dynein, a two-headed motor protein, was found to act processively in its interaction with microtubules (Wang, 1995). Whether the individual motor domains are capable of sustained force production or processive behavior remains to be determined. A single-headed form of flagellar dynein was subsequently reported to produce force processively (Sakakibara, 1999). It is uncertain whether this feature is a special evolutionary adaptation of this molecule. The dynein molecules were randomly adsorbed to coverslips using a simple adsorption method performed at low protein concentrations. Although the distribution of particles was confirmed by TIRF microscopy using a fluorescent ATP analogue, aggregates of dynein are not readily detected. Furthermore, this method detects fully active dynein, but so-called "dead-heads," which fail to bind ATP but bind microtubules strongly, would be missed.

The rat cytoplasmic dynein motor domain has been expressed using baculovirus infection of insect cells. Full-length dynein heavy chain has also been expressed and purified. Although it had some tendency to aggregate, full-length dynein HC was found to have limited motility activity (Mazumdar, 1996). A construct of about 350 kDa corresponding to the complete motor domain, and lacking the projecting microtubule-binding region, referred to as the stalk (Gee, 1997) has also been produced. Each of these constructs has a hexahistidine and an epitope tag, which is used for purification and/or linkage to the nanoarray supports. Both constructs act as unique species by sedimentation and sizing chromatography, and have high levels of ATPase activity. The motor domain construct binds microtubules efficiently, which are released using ATP. These properties are strongly consistent with mechanochemical activity.

Additional experiments include testing for microtubule activation of the ATPase activity, a further sign of motor activity. Microtubule gliding assays, in which the motor domains are adsorbed at high density to coverslips, are performed as a more direct test for force production. The motor domains are then attached to $Ni^{2+}$ posts. The spacing between posts is varied to test whether the motor domains act alone or cooperatively. If spacing of less than about 12 nm (i.e., the diameter of the motor domain) is required for full microtubule gliding activity, this suggests that two motor domains must act in concert. If the spacing must be even shorter than this distance, it suggests that the motor domains interact through the flat top or bottom surfaces of the AAA rings. A compact morphology for the two cytoplasmic dynein motor domains has been observed in one study (Amos, 1989), though no direct evidence for such an interaction between dynein motor domains has been forthcoming. If the motor domains are functional at greater spacing, this will provide evidence that the individual domains are functional. In order to ensure no more than one motor domain per microtubule, short microtubules (about 1 μm) are applied to nanoarrays bearing dynein motor domains at even greater spacing.

If the motor domain fails at any spacing to support microtubule gliding activity, this means that the peptide tag being used may be located at a suboptimal site. Versions of the motor domain with tags at each end are then tested. Different modes of attachment are also tested, for example using antibody against the epitope tag to increase the flexibility and length of the link to the coverslip.

If motility is observed using both motor domain constructs, it is of considerable interest to compare the step size obtained in each case. Based on single particle image averaging of dynein electron micrographs, it is proposed that the power stroke primarily involves a shift in the interaction between the stem and the AAA ring, and secondarily between the microtubule-binding stalk and the AAA ring. By measuring the step size for each construct (Gelles, 1988; Wang, 1995), the present inventors are able to test directly which portion of the motor domain makes the more significant contribution, and, in turn, gain valuable new insight into how the motor domain functions.

Numerous fragments of the cytoplasmic dynein heavy chain using both baculovirus infection of insect cells and transformation of bacterial cells for recombinant protein production have been produced to analyze dynein function. Of particular interest is the full motor domain construct, which contains all of the elements thought to be required for force production. This construct is being produced in milligram quantities with either a hexahistidine or FLAG epitope tag. At least two types of experimental set-ups are possible using ordered nanoarrays. First, the dynein motor domain is attached to $Ni^{2+}$ bearing dots through the hexahistidine tag synthesized as part of the full motor domain construct. Microtubules are applied to the array in the presence of ATP, and microtubule gliding motility is evaluated and quantified as a function of dot spacing. These experiments provide new insight into whether dynein motor domains function by a cooperative mechanism and how the optimal spacing between motor domains compares with the spacing between tubulin subunits in the microtubule lattice. The nanoarrays of dynein are also tested for their ability to seed crystallization, as a first step toward determining the structure of the motor domain at atomic resolution.

To test for the important spacing in the substrate array, tubulin and tubulin fragments are linked to the dots within the naoarray. Initially, tubulin dimers are linked by hexahistidine tags to Ni-NTA dots, giving a random orientation of the dimers. A similar experiment is performed with hexahistidine actin to look for myosin binding. To look for more detailed aspects of the binding and the motility, an oriented array of tubulin dimers is developed. Hexahistidine is used for one subunit and cysteines used for the other subunit. Cysteine reacts with gold and hexahistidine reacts with Ni-NTA dots, respectively. The gold and Ni-NTA posts are successively stamped on the substrate with a directed 5 nm displacement.

For measurement of binding and possibly mobility, the dynein motor domain is bound to latex beads or native dimers will be purified. The beads or dynein dimers are applied to the nanoarrays and tested for binding or dynein-mediated movement. These experiments determine the spacing of the tubulin binding sites, step size inherent in the dynein crossbridge cycle, and whether the motor protein can accommodate to an imperfect lattice and still produce force.

Analysis of Integrin and Actin Interactions as a Function of Spacing

There are many large cytoskeletal proteins with multiple binding sites that are spaced by 20-100 nm (see Djinovic-Carugo, K. et al. (2002) *FEBS Lett.*, 513:119-23; Goldmann, W. H. et al. (1996) *J. Muscle Res. Cell Motil.*, 17:1-5; Liu, S. et al. (1997) *Eur. J. Biochem.*, 243:430-6). These proteins have critical functions in cells and tissues that depend upon their specific binding to other components. We are exploring the spatial dependence of their binding interactions by measuring their relative interaction with different arrays of their binding partners. Theoretical analyses suggest that the proper spacing can increase binding avidity by orders of magnitude.

Nanofabricated arrays now make it possible to measure the exact spatial dependence of the binding interactions. As one example, we are exploring the spatial dependence of integrin and actin arrays on their interactions with a variety of binding partners both in vivo and in vitro.

There is considerable evidence that the spacing between liganded integrins strongly affects binding to cytoplasmic proteins such as talin. For example, the binding of a fibronectin trimer causes specific attachment of talin1 to the cytoplasmic tail of integrin avb3. Talin1 is an anti-parallel dimer with both actin and integrin binding sites that has an overall length of about 50 nm whereas the fibronectin-integrin binding sites on the trimer are 40-70 nm apart. One explanation for the specific binding of the trimer to the actin cytoskeleton is that the spacing of the liganded integrins matches the spacing of the talin1 integrin binding sites. To test for this, arrays of cytoplasmic domains of integrins with different spacings are created. If a particular spacing binds GFP-talin1 more avidly than other spacings, a determination is made as to whether this corresponds to the full length of the talin1 dimer or to some other parameter of the molecule.

More specifically, recent studies indicate that the spacing of integrins and of actin is critical for the specific binding of many proteins (Calderwood, D. A. and M. H. Ginsberg (2003) *Nat. Cell Biol.*, 5:694-97). For example, a single trimer of fibronectin (FIG. 1(*a*)) forms a slip bond with the cytoskeleton (FIG. 1(*b*)), whereas randomly spaced monomers of fibronectin do not (Jiang, G. et al. (2003) *Nature*, 424:334-37). A critical aspect of forming slip bonds is the selective binding of talin1. Talin1 is an anti-parallel dimer with an overall length of 56 nm (Winkler, J. et al. (1997) *Eur. J. Biochem.*, 243:430-36). Since talin has an integrin binding site at the N-terminal end and an actin binding site at the C-terminus, an optimal spacing for beta integrin binding at both sites is theoretically about 50 nm. In the fibronectin trimer, the spacing between the pairs of RGD binding sequences is maximally about 60 nm (Coussen, F. et al. (2002) *J. Cell Sci.*, 115:2581-90). The match between the spacing of the binding sites on the outside of the cell and those on the inside is very good and could be an important factor in creating the specific binding complexes. Indeed, the trimer rapidly forms a slip bond to the cytoskeleton that is broken at a force of 2 pNewton whereas monomer-coated beads bind more slowly and don't show preferential breaking at 2 pN. Applicants believe that the spacing of the monomeric integrins on beads varied and was often much greater than can be spanned by talin1. The present invention enables placing fibronectins or integrins at specific spacings on a surface. The optimal spacing can be determined by in vitro and in vivo testing.

Cells bind to extracellular matrix-coated glass differently than to the same matrices in three dimensions, as a result of the spatial organization of matrix subunits. We are analyzing cell spreading on different arrays of fibronectin with defined spacings in the range of 20-150 nm. Initially, we will prepare substrates with 30 micron squares with a given array of fibronectin to allow cells to bind to that array. We start with a small spacing and increase the spacing to determine the maximum separation that allows binding. Pairs of gold dots (2-5 nm in diameter) are centered in 150×300 nm areas and the spacing between the dots is varied from 25 to 150 nm. Other arrays with rows of dots spaced by 20-150 nm are formed at a row-to-row spacing of 150 nm. Stamping technology produces more closely spaced rows (giving square arrays from 20×20 nm). The order in the arrays produces order in the cell spreading process. Cell spreading analysis enables us to quantitatively analyze the effect of order on spreading. The spreading process of talin1 mutant cell lines and other cell lines are also investigated.

There are many actin binding and integrin binding proteins that have an anti-parallel dimer structure (see Dhermy, D. (1991) *Biol. Cell.*, 71:249-54; Goldmann, W. H. et al. (1996) *J. Muscle Res. Cell Motil.*, 17:1-5; Liu, S. et al. (2000) *Eur. J. Biochem.*, 243:430-6). The length of these molecules is somewhat variable because they are often composed of repeated domains such as the spectrin domains that have flexible linkages between the domains. Theoretically, alpha actinin can span about 60 nm whereas the larger talin molecule can span over 100 nm and is reported to have 4 binding sites for beta 1 and 3 integrin cytoplasmic tails. Since it is believed that talin causes a separation of the alpha and beta tails, it is likely that the isolated beta cytoplasmic domains will be capable of binding talin. For in vitro experiments, the device has smaller areas (1.5×3 μm) with the same spacings of the gold posts. This gives 100 binding pairs over that area, which can be viewed readily in TIRF.

The array of posts on a clean glass surface are prepared and then the open areas of glass are reacted with PEG-sylanizing reagent to prevent non-specific absorption of the protein. To ensure the proper orientation of the bound proteins we express the beta cytoplasmic tails in bacteria with a construct that places biotin on the amino terminus, which faces the membrane. Avidin is bound to the gold dots and then the biotin fragments will be added. Initially, we saturate the sites with biotin to examine the effect of spacing. Addition of a cysteine in the N-terminal region of the peptide enables us to fluorescently tag the fragment and then assay the density of bound cytoplasmic fragments in regions with single 5 nm gold dots spaced by over 0.5 micron from other dots. Images of single fluorophores are quantified to determine the average number of fluorophores per dot, using the intensity and the bleaching characteristics, since bleaching of one of two fluorophores cuts the intensity in half, while single fluorophores blink out. Similarly, binding regions are manifest as a function of incremental changes in fluorescence level.

Fabrication of Nanoarray Devices

Applicants have developed a coherent strategy for the preparation of nanoscale patterns for the study of biological molecules. The methods demonstrate an extremely high level or precision and control at the nanometer regime.

This work takes advantage of metal and semiconductor processing on scales that match the size and/or spacing of features of specific protein or subcellular protein complexes, some of which have dimensions of only a few nanometers. In order to create these structures, multiple approaches are pursued: electron beam lithography, nanoimprinting lithography, contact printing, and directed self-assembly.

For the applications herein, hierarchical arrays of diverse materials to which specific proteins can bind, are patterned on a transparent substrate. The arrays consist of unit cells comprised of small numbers (about 2-4) of metal dots separated from one another by distances of about 10-200 nm and in some cases arranged in specific spatial configurations according to certain crystallographic space groups. Each array contains a sufficient number of posts within an area of about 1-5 micrometers so as to be easily detected by TIRF microscopy. Permutations on the dot spacing and/or the precise spatial configuration of the dots in each unit cell form the next level of hierarchy in the arrays, which cover areas of several micrometers to several millimeters. Such hierarchical arrays cannot be created exclusively by chemical self-assembly techniques, which are better suited to applications requiring vast numbers of identical elements, but with little or no long range order and no simple way of varying the intra-unit cell spacing. Instead, more conventional "top down" lithographic techniques is used, which have the flexibility to form patterns comprising many different unit cell variations.

Top-down fabrication of these bioarrays is a significant challenge, because the required dimensions (both the feature size and spacing) are near the current limits of lithographic patterning techniques. As an example, ultrahigh resolution electron beam lithography, with precise exposure dose control for critical features, and the use of small radius of gyration resist materials with low temperature processes that enhance resolution and maintain contrast extends the limits of these techniques. The patterns are transferred by liftoff and/or ion beam etching to metals for which the binding chemistry of various biological molecules is known. For certain applications, arrays comprising diverse chemical species may be of interest. For such applications, multiple lithographic steps can be used with ultrahigh placement accuracy to pattern arrays of dissimilar metals (for example, gold dots followed by nickel dots could create a pattern for binding sulfhydryl and poly-histidine tags, respectively). As another example, patterning is achieved by scanning probe lithography, including dip-pen, x-ray, or extreme UV lithography, and contact printing.

Figure 2:
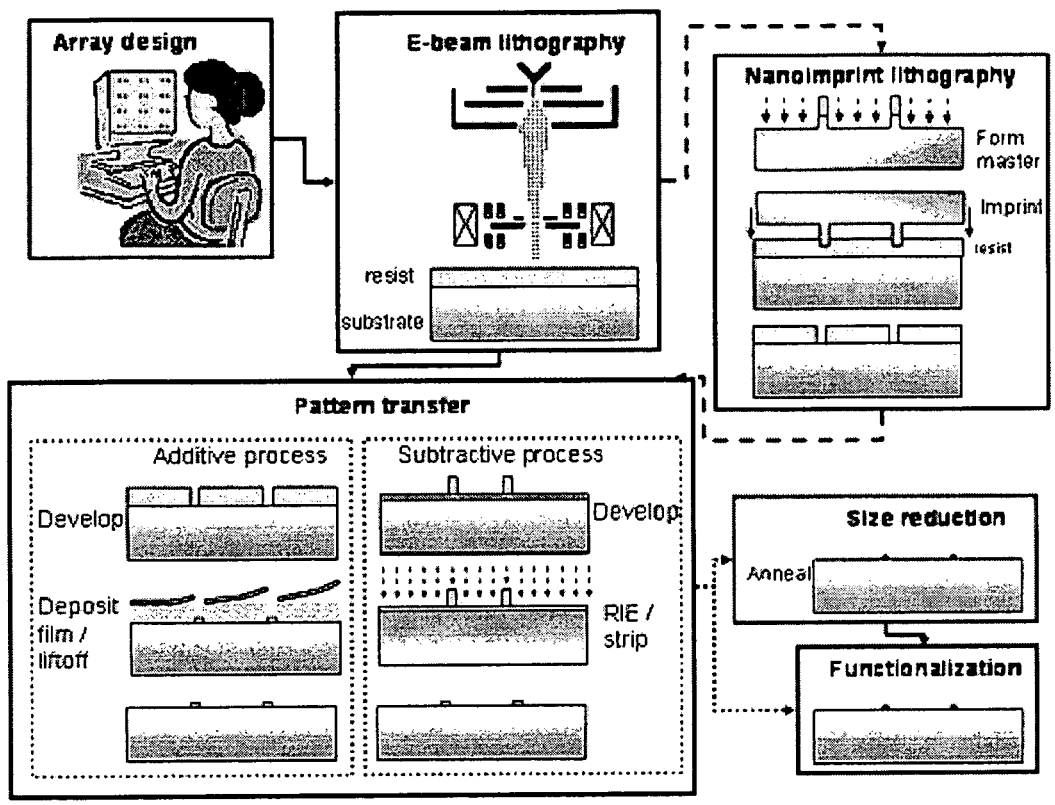
FIG. 2 depicts a proposed process flow for the fabrication of a device according to the present invention.

A proposed process flow for the fabrication of hierarchical bioarrays with molecular spacings is shown in FIG. 2. First, arrays are designed using either a generic CAD package or an algorithmic design system, allowing for the systematic variation of unit cell configuration and spacing. The design data are used as input to a high resolution electron beam lithography (e-beam) system, which writes each pattern onto a transparent substrate coated with a radiation sensitive layer (resist). In the high throughput phase of the program, e-beam lithography is used to pattern a mask, from which the array patterns are subsequently transferred by nanoimprint lithography, described below. Depending upon the details of the pattern transfer process, either a positive or negative tone resist is used. Pattern transfer then takes place via an additive process, such as liftoff or electroplating, or via a subtractive process, such as reactive ion etching, ion milling or controlled wet etching, depending upon the selected materials. Once metal dots have been formed on the substrate, subsequent processing depends upon the precise application. For example, for the investigation of protein binding, microfluidic channels are formed, and ligands are bound to the appropriate dots on the array. After washing and blocking the rest of the surface to prevent non-specific interactions, the binding molecules tagged with an appropriate fluorophore are added through the flow channel, incubated to allow binding, and washed out to measure release. A linker molecule is introduced which adheres to the metal by chemical bonding. For protein crystallization experiments, the arrays are used with or without further processing.

Figure 3:
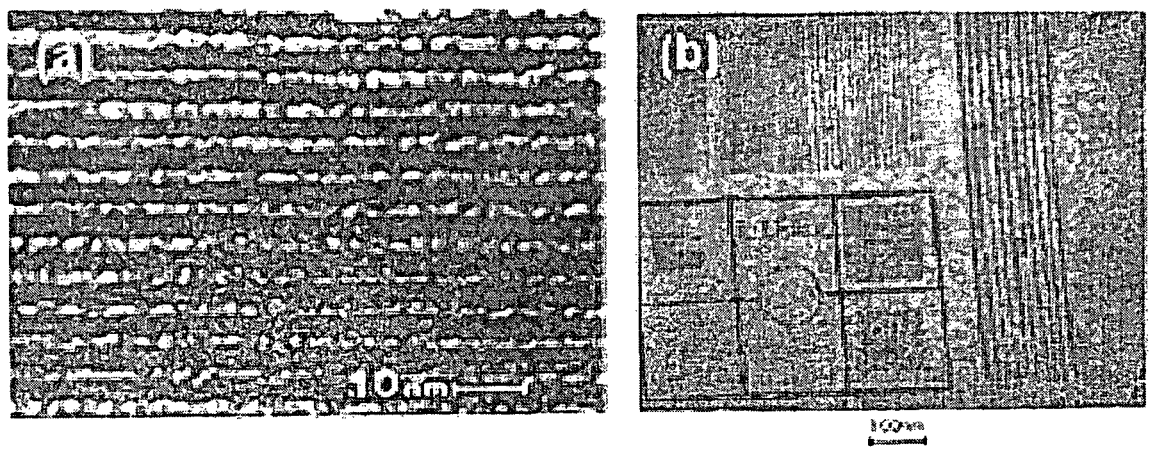
FIG. 3 depicts features with nanometer scale dimensions patterned by electron beam lithography.
Figure 4:
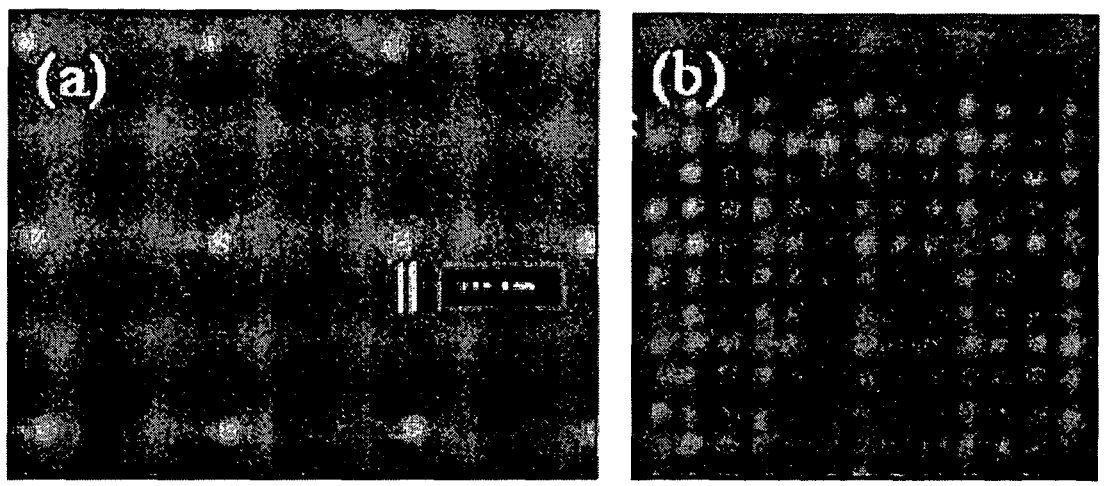
FIG. 4 shows arrays of dots of hydrogen silsequioxane, a negative tone electron beam resist.

A prevailing myth exists which essentially holds that top-down patterning (i.e., conventional lithography) cannot be used to form features smaller than about 10 nm and arrays with center-to-center spacings less than about 50 nm (Broers, A. N. (1988) *IBM J. Research and Dev't*, 32(4):502-513). As can be seen in FIG. 3, as early as 1981, features with nm-scale dimensions have been patterned by electron beam lithography (Isaacson, M. and A. Murray (1981) *J. Vacuum Sci. Tech.*, 19(4):1117-1120), and arrays with pitches of about 10 nm have been realized (Langheinrich, W. and H. Beneking (1993) *Jap. J. App. Physics Part 1—Reg. Papers Short Notes Rev. Papers*, 32(12B):6218-6223). FIG. 3(*a*) shows sub-5 nm lines patterned in NaCl film by electron beam-induced vaporization as in Isaacson and Murray, 1981. FIG. 3(*b*) shows sub-10 nm pitch lines patterned in Al-doped LiF, also as in Isaacson and Murray, 1981. In each case, exceedingly high doses were required, and pattern transfer was problematic. Until recently, the key challenges in accessing the sub-10 nm regime have been in identifying practical lithographic materials with sensitivities that allow for manageable exposure times and are amenable to direct pattern transfer. Such materials have recently been discovered (Namatsu, H. et al. (1998) *J. Vacuum Sci. Tech.*, 16(6):3315-3321; Rooks, M. J. and A. Aviram (1999) *J. Vacuum Sci. Tech. B*, 17(6):3394-3397; Yasin, S. et al. (2001) *App. Physics Lett.*, 78(18):2760-2762), and new approaches to processing (Yasin, S. et al. (2001) *J. Vacuum Sci. Tech. B*, 19(1):311-313) are also extending the resolution of commonly used electron beam resists, such as PMMA. The e-beam system is an FEI scanning electron microscope fitted with Nabity e-beam lithography control system. Lithography can be done at energies between 1-30 keV, and the system has already demonstrated sub-10 nm patterning capability, although low probe current limits practical pattern density and coverage for large arrays. The Leica VB-6HR is generally operated at 100 keV. This system has sufficient probe current to pattern arrays spanning many mm in a reasonable exposure time, and it has also shown sub-10 nm patterning capability, and sub 5-nm patterning capabilities are being pursued. FIG. 4 shows arrays of dots of hydrogen silsequioxane (HSQ), a negative tone electron beam resist. FIG. 4(*a*) shows ultrahigh resolution patterning of 6 nm HSQ dots on 100 nm pitch, while FIG. 4(*b*) shows a 25 nm pitch n×n array. Relatively isolated features as small as 6 nm have been patterned, and dense arrays, with center-to-center spacing down to 25 nm have already been achieved. Such high resolution is possible because of the cage-like structure of the HSQ molecule (Siew, Y. K. et al. (2000) *J. Electrochem. Soc.*, 147(1):335-339) and its small radius of gyration (Namatsu, H. et al. (1998) *J. Vacuum Sci. Tech. B*, 16(1):69-76). Reducing the molecular weight of the material is likely to result in further improvements in "raw resolution." HSQ can be easily converted to $SiO_2$ by thermal treatment or by exposure to an oxygen plasma, so that careful etching in dilute hydrogen fluoride (HF) can be used to reduce the dimensions of the dots even further. The dots can be used as a mask to transfer the pattern into an underlying film of metal or other material to which the selected proteins can bind, by ion milling or reactive ion etching.

Figure 5:
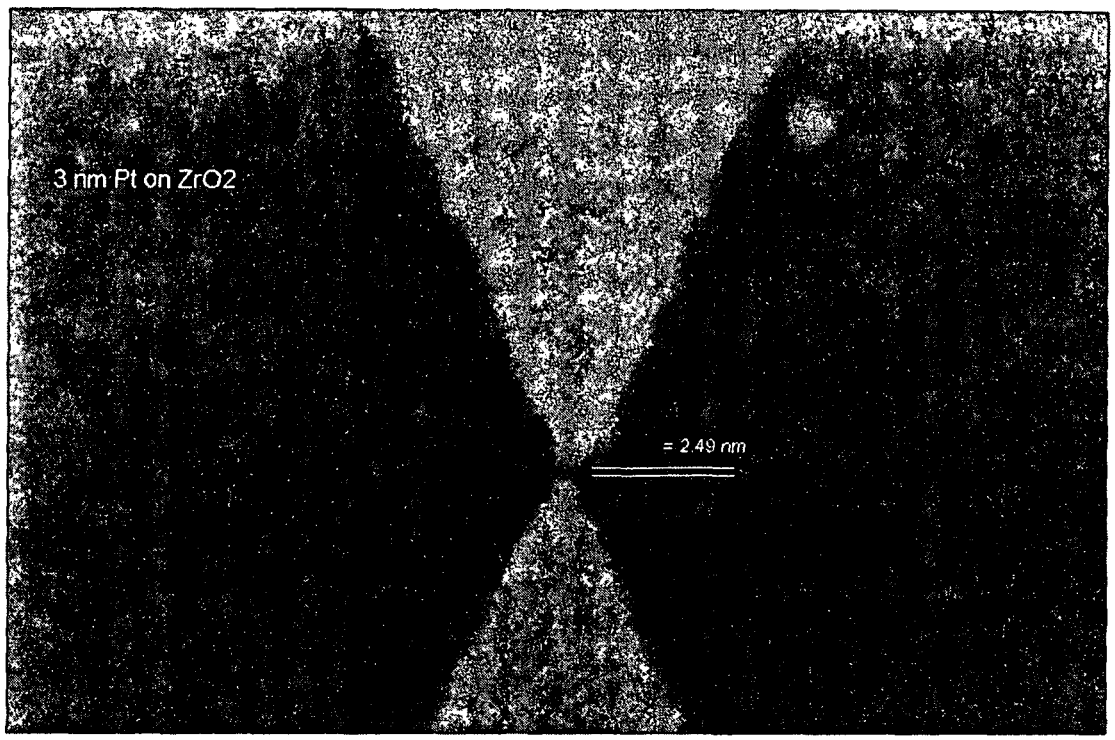
FIG. 5 depicts an electrode pair for the study of transport in individual molecules fabricated by direct-write e-beam lithography.
Figure 6:
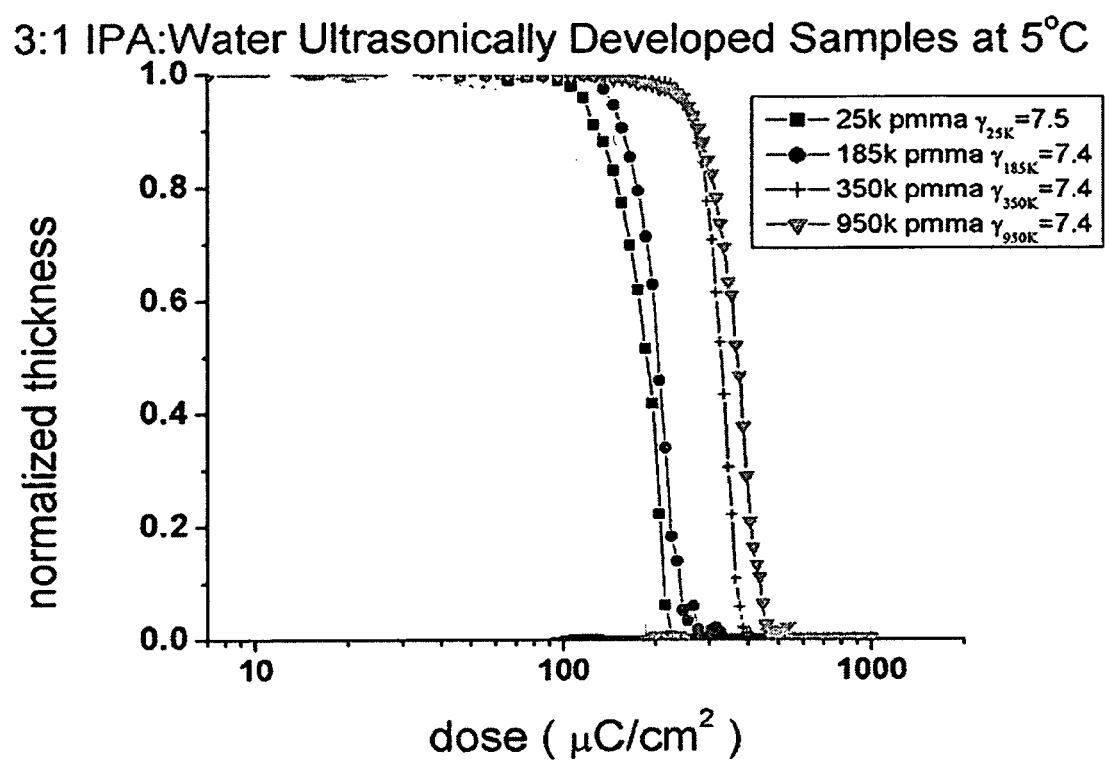
FIG. 6 is a graphic representation of resist thickness as a function of applied dose for a 3:1 isopropanol:water mixture using various molecular weights of poly(methyl)methacrylate.
Figure 7:
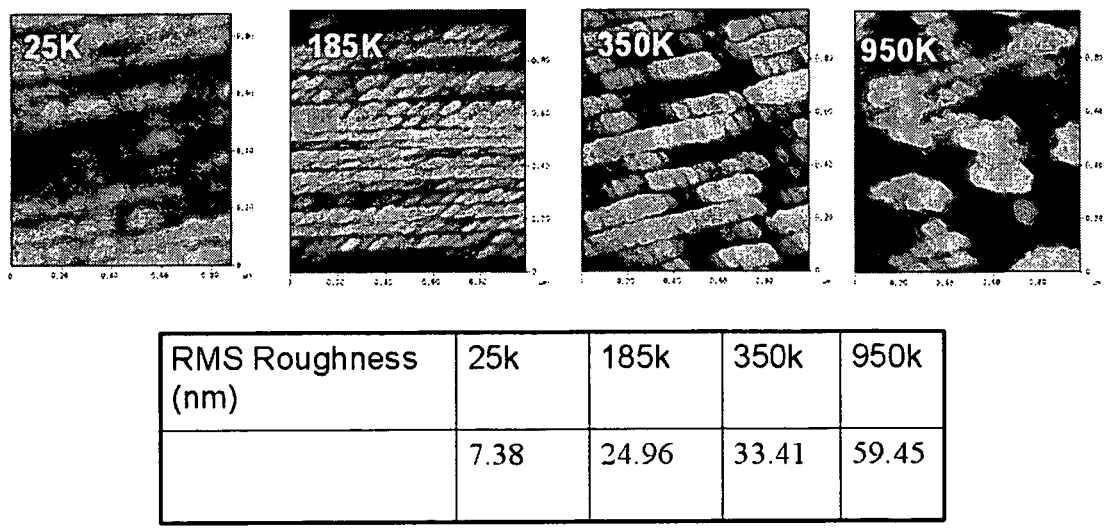
FIG. 7 shows surface roughness of PMMA as a function of molecular weight.

In addition to HSQ, resolution enhancing processes in the positive tone resist PMMA can be performed. As mentioned above, Yasin et al. (Yasin, S. et al. (2001) *App. Physics Lett.*, 78(18):2760-2762) have demonstrated about 5 nm patterning capability by use of a new resist development process using two nonsolvents, isopropanol and water, combined with ultrasonic agitation. This new process offers superior contrast and resolution when compared to the conventional developer dilute methyl-isobutyl-ketone (in IPA). It appears that IPA and water combine to form a co-solvent which is able to more efficiently penetrate the polymer matrix with minimum resist swelling (which normally leads to a loss of resolution). The ultrasonic agitation induces microstreaming, yielding an efficient mechanism for providing fresh developer to the polymer and rapid removal of dissolved material. Following Rooks et al., (Rooks, M. J. et al. (2002) *J. Vacuum Sci. Tech. B*, 20(6): 2937-2941), this process was improved by reducing the developer temperature, resulting in increased contrast relative to room temperature development (as well as conventional developers) (Rooks, M. J. et al. (2002) *J. Vacuum Sci. Tech. B.* 20(6):2937-2941). This process is employed for the fabrication of electrodes for the study of molecular electronics, an example of which is shown in FIG. 5, with sub-5 nm spacing. FIG. 5 shows a an electrode pair for the study of transport in individual molecules fabricated by direct-write e-beam lithography and low temperature ultrasonic development using an IPA:H$_2$O mixture. We are extending both the resolution and reliability of this process by the use of low molecular weight PMMA. Initial experiments (Greci (2003) private communication) indicate that low temperature development using an IPA/water mixture with ultrasonic agitation maintains the resist contrast even as the molecular weight is reduced, as shown in FIG. 6. FIG. 6 shows the remaining resist thickness as a function of applied dose for a fixed development time, for four different molecular weights of PMMA. As can be seen in FIG. 6, contrast does not degrade with a reduction in molecular weight when for used for ultrasonically assisted low temperature using an IPA:H$_2$O mixture. This is strikingly different from what is found using conventional developers (i.e., MIBK solutions), where both contrast and resolution suffer when low Mw is used (Dobisz, E. A. et al. (2000) *J. Vacuum Sci. Tech. B.* 18(1):107-111). In addition, scanning probe analysis of partially developed resist shows that the low molecular weight has significantly lower surface roughness than the higher molecular weight material when processed using low temperature ultrasonic development, as shown in FIG. 7. FIG. 7 shows atomic force micrographs of partially developed PMMA of different molecular weights. Reduced surface roughness has been shown to correlate with improved resolution (Namatsu, H. et al. (1998) *J. Vacuum Sci. Tech. B,* 16(6):3315-3321; Yasin, S. et al. (2001) *J. Vacuum Sci. Tech. B,* 19(1):311-313), and preliminary experiments indicate that improved resolution and linewidth control are indeed achieved with low molecular weight PMMA.

When a positive tone resist, such as PMMA, is used for the fabrication of bioarrays, pattern transfer is achieved by liftoff or by electro- and electroless plating. One challenge in using such processes at this size scale is the control of the metal grain structure, which, for some metals, can approach the targeted feature size. The electron beam evaporation system has sub-nanometer thickness control and liquid nitrogen-cooled stage, offering the possibility of ultrafine grain metal deposition. When a negative tone resist, such as HSQ, is used, the pattern transfer is done by etching—reactive ion etching, ion milling, or carefully controlled wet chemical etching, depending on the materials involved.

Figure 8:
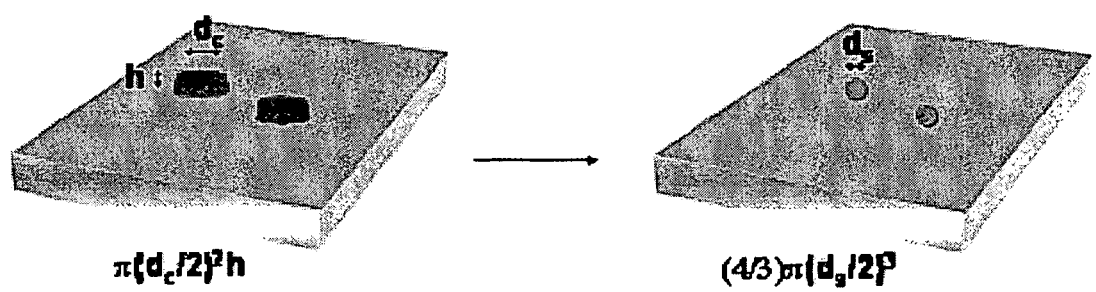
FIG. 8 illustrates the reduction of dot size by thermal treatment.

Once dots with sub-10 nm have been formed, further dimensional reduction can be achieved as illustrated by the thermal treatment depicted in FIG. 8. After lithography and pattern transfer, each metal dot approximates a cylindrical disc sitting on the substrate. Thermal treatment causes the dots to minimize their surface area, forming spheroids. Reduction of the dot thickness to a fraction of its diameter results in a significant reduction in the final dot size. For example, a dot with a diameter of 6 nm and a thickness of 0.5 nm is reduced to about a 3 nm sphere. For this approach, precise control over film thickness and grain structure is also important. Table 1 tabulates the reduction in dimensions depicted in FIG. 8.

TABLE 1

Dimensional Reduction by Thermal Treatment

| $d_c$ (nm) | h (nm) | $d_s$ (nm) |
|---|---|---|
| 10 | 1 | 3.9 |
| 10 | 0.5 | 3.0 |
| 8 | 1 | 3.3 |
| 8 | 0.5 | 2.6 |

Figure 9:
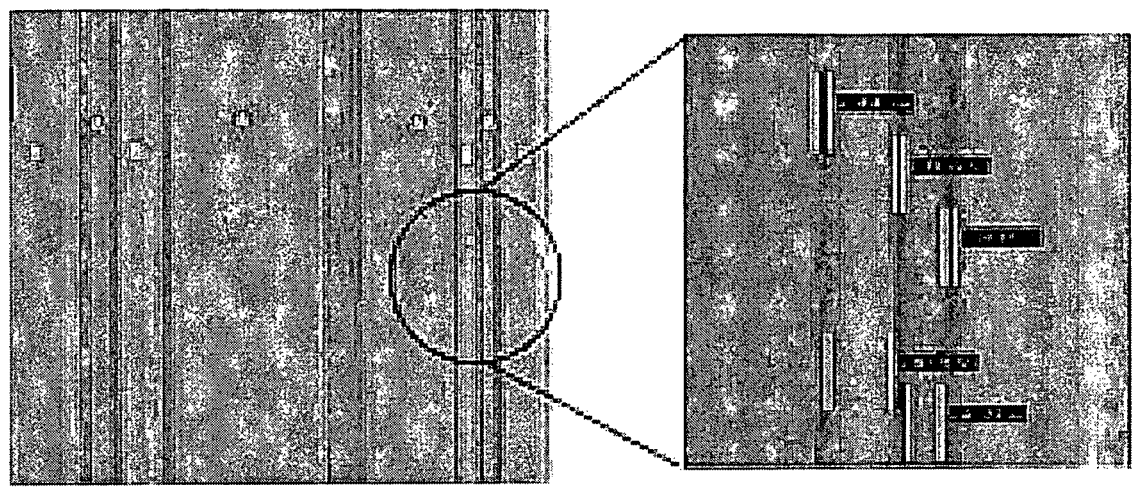
FIG. 9 gives an example of high resolution placement accuracy e-beam lithography.

For certain applications, it is desirable to form patterns of closely spaced posts of different materials, such as gold and nickel-NTA. In this case, two levels of lithography is required, with level-to-level overlay of about 10 nm. Such placement accuracy is achievable with e-beam lithography using careful alignment strategies (Guillorn, M. A. et al. (2000) *J. Vacuum Sci. Tech. B,* 18(3):1177-1181). As an example, FIG. 9 shows a set of four interdigitated metal lines in which successive pairs of alternative lines were patterned in separate lithographic exposures and metal depositions (Wind, S. J. et al. (2003) *J. Vacuum Sci. Tech. B*, accepted for publication). Through high-resolution placement accuracy using e-beam lithography, levels A and B depicted in FIG. 9 were patterned and processed separately. The enlargement on the right in FIG. 9 shows better than 5 nm overlay.

Figure 10:
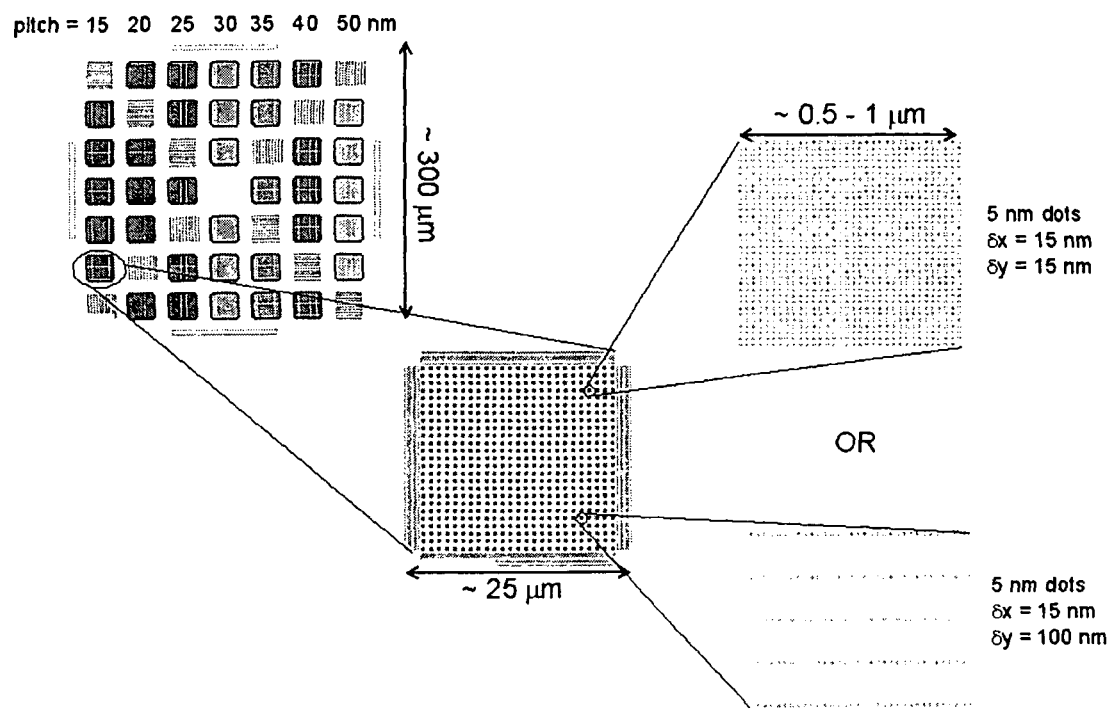
FIG. 10 depicts an exemplary device according to the present invention.

FIG. 10 depicts an exemplary device fabricated by the above process.

Figure 11:
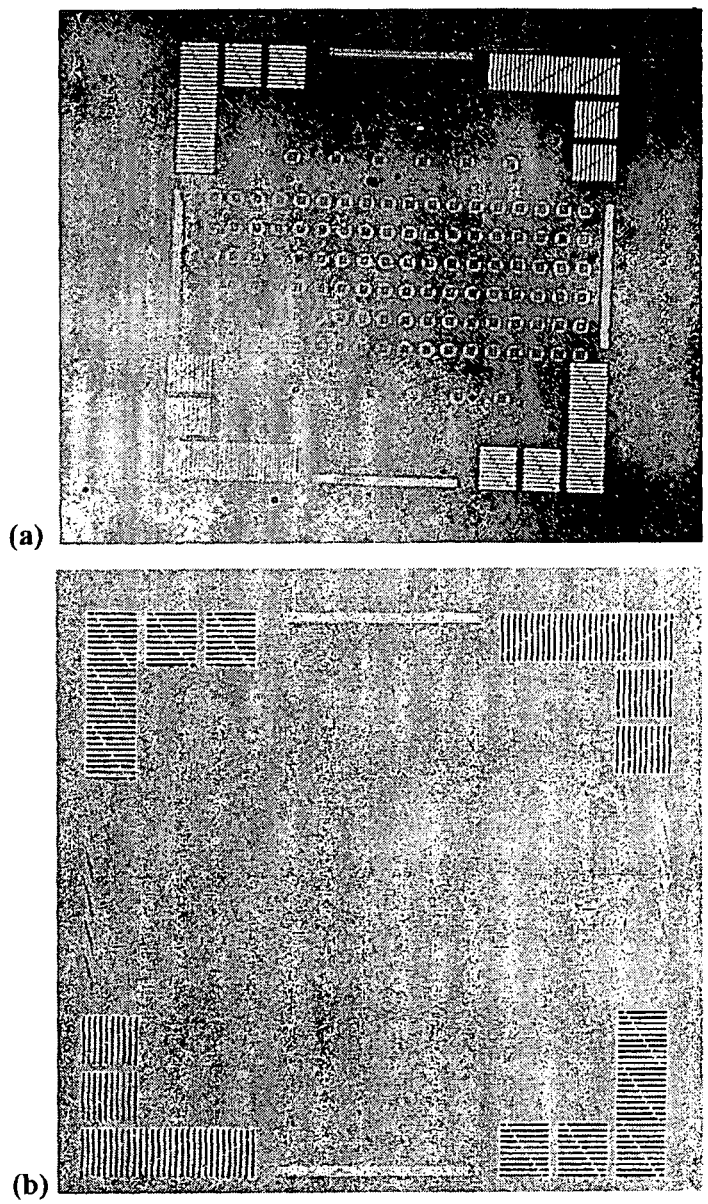
FIG. 11 depicts micrographs of a prototype chip with patterned arrays according to the present invention.

FIG. 11 depicts an optical electron micrograph (FIG. 11(*a*)) and a scanning electron micrograph (FIG. 11(*b*)) of a prototype chip with patterned arrays according to the present invention. The micrographs are each about 300 microns square. The circular frames around each of the arrays are visible in FIG. 11(*a*).

Figure 12:
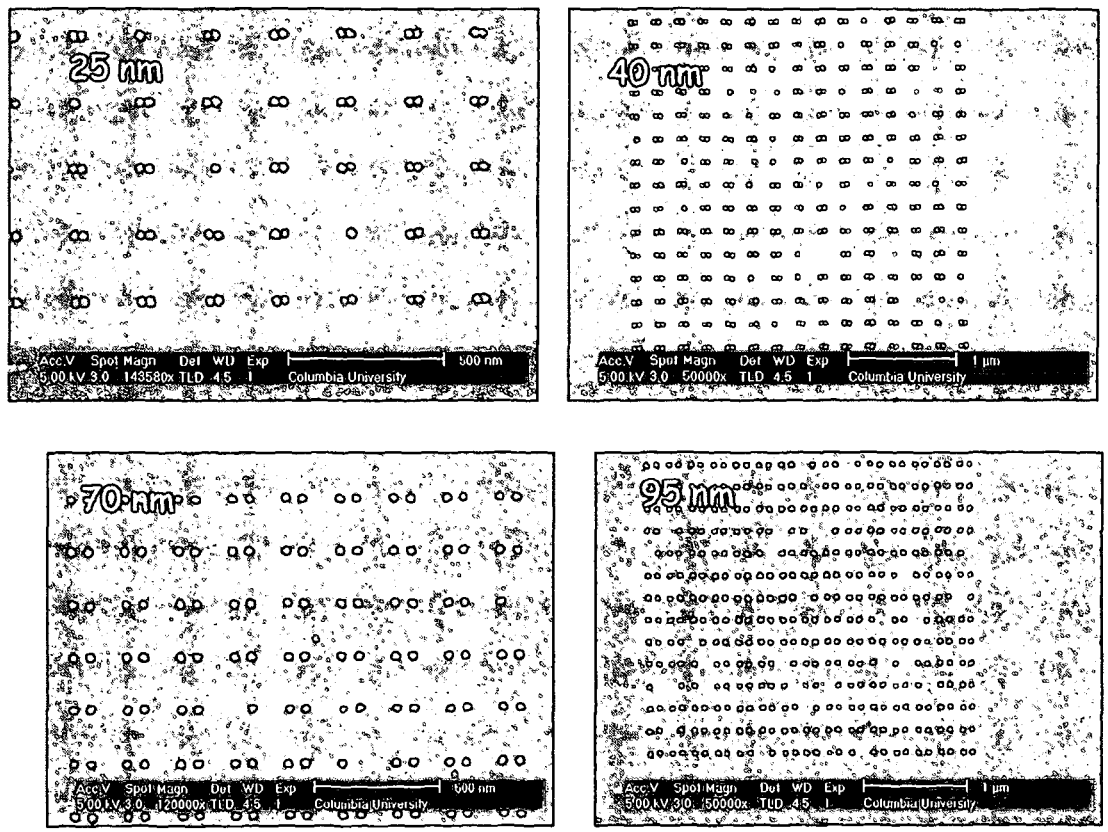
FIG. 12 depicts prototype dot pair arrays according to the present invention.

FIG. 12 depicts prototype dot pair arrays fabricated by the above process.

Figure 13:
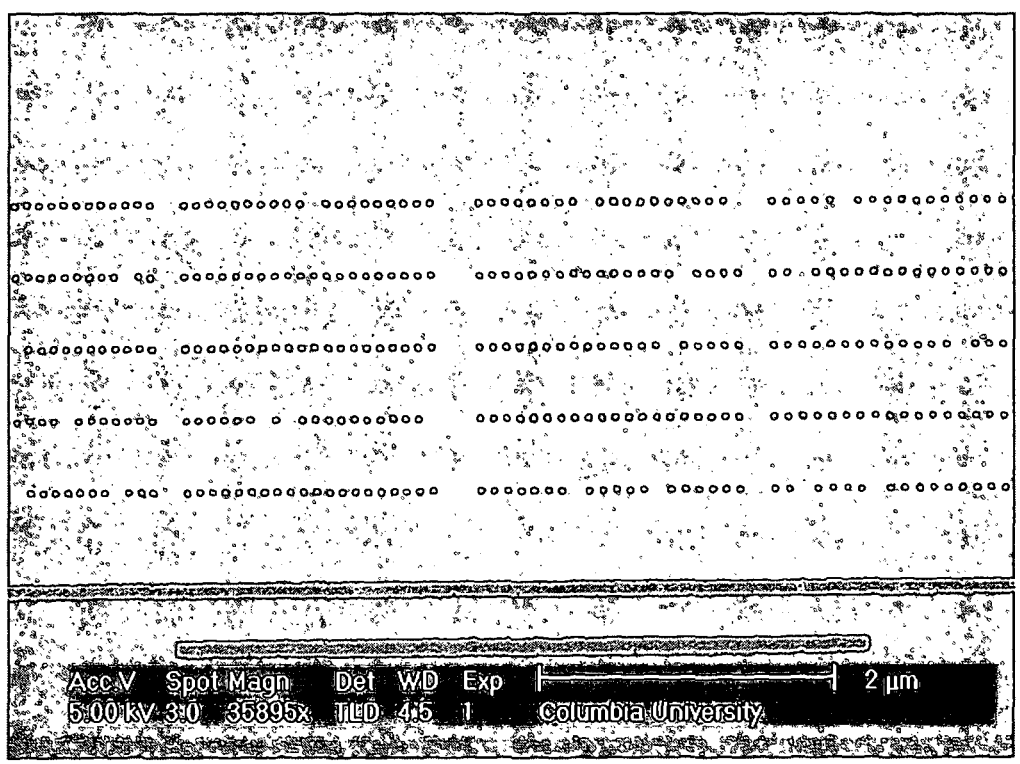
FIG. 13 shows a prototype dot array according to the present invention.

FIG. 13 shows a prototype dot array fabricated by the above process, and demonstrates a linear array of dot strings having specific spacings.

Figure 14:
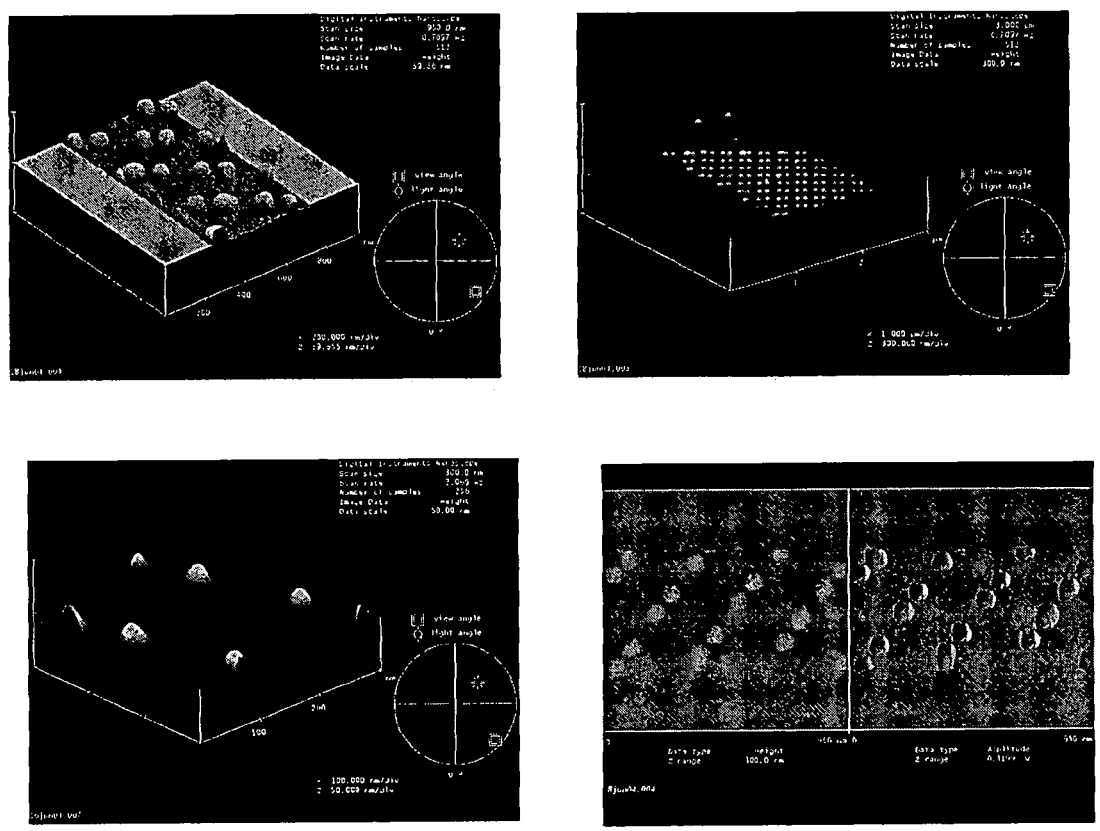
FIG. 14 depicts atomic force microscopy of prototype arrays according to the present invention.

FIG. 14 depicts atomic force microscopy of gold-patterned prototype arrays fabricated by the above process.

Figure 15:
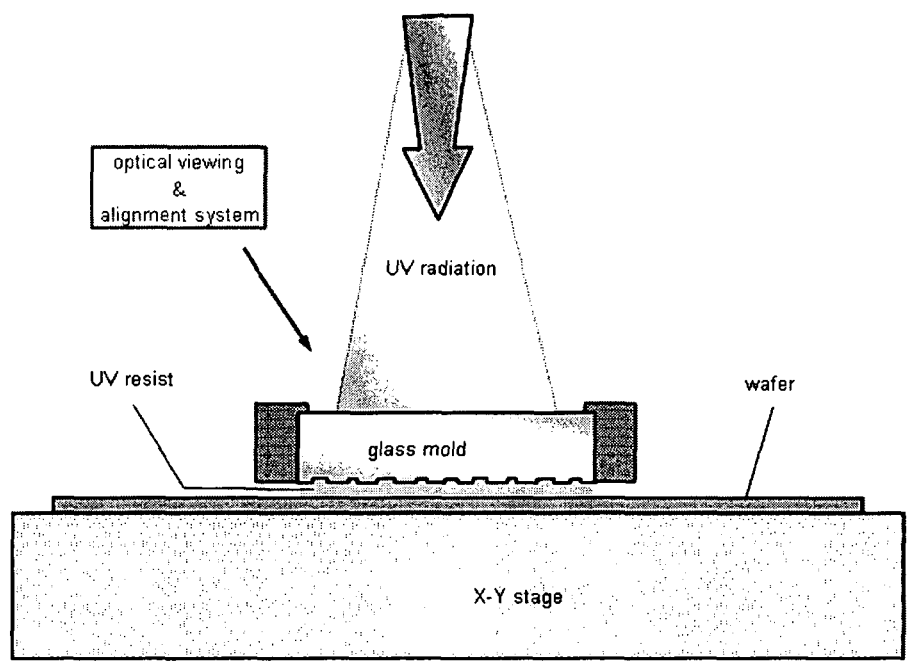
FIG. 15 shows a system for fabricating exemplary devices according to the present invention.
Figure 16:
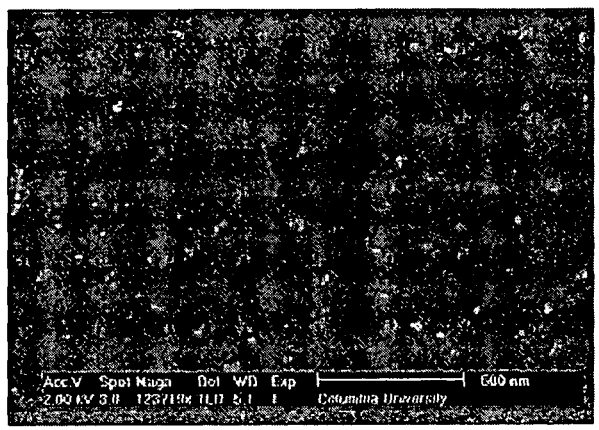
FIG. 16 shows lithographic ways of patterning according to the present invention.
Figure 16:
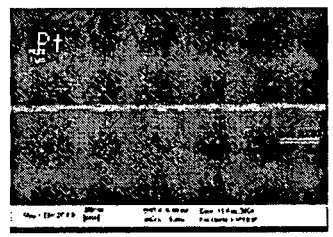
Figure 16:
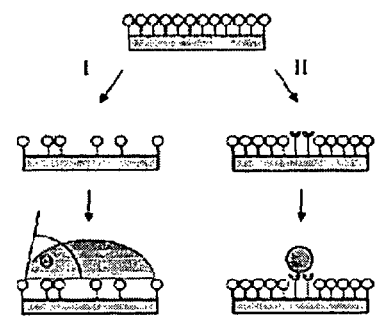

Since direct write electron beam lithography is a low throughput serial process, it is not suitable for the production of large numbers of array samples. Therefore, the use of nanoimprint lithography, which has the potential for use as a manufacturing vehicle, is an alternative. FIG. 15 depicts a system for mass-producing a device using nanoimprint lithography. Other lithographic alternatives for patterning include PMMA, platinum, and direct patterning of self-assembled monolayers, as depicted in FIG. 16.

While the invention has been described in detail with reference to certain embodiments thereof, it will be understood that the invention is not limited to these embodiments. Indeed, modifications and variations are within the spirit and scope of that which is described and claimed.

What is claimed is:

1. A device comprising:
   (a) a substrate having a surface; and
   (b) regions on the surface, each region separately comprising an ordered, two-dimensional array of post sets over the surface, wherein the pitch between adjacent posts within each post set of a region is uniform and is less than about 100 nm, and wherein each post has affixed thereto a ligand or protein molecule that comprises at least a portion of a full-length tubulin;
   but the device comprises a gradient of pitch values from one region to another, designed for measuring the spatial dependence of binding of one analyte molecule to a post set within at least one region;
   wherein the pitch is the distance between center points of adjacent posts in a post set and the gradient is a gradual change in the pitch values in the different regions such that the distance between posts in a post set in at least one region matches the spacing and distribution of binding sites in a complex that forms between the one analyte molecule and two ligands or protein molecules on different posts within a post set.

2. The device of claim 1, wherein the gradient of pitch values is about 5 nm to about 100 nm.

3. A method of identifying the presence of an analyte from a fluid sample, the method comprising (a) providing a device comprising a substrate having a surface; the surface comprising regions, each region comprising an ordered, two-dimensional array of post sets over the surface, where the pitch between adjacent posts within each post set within a region is uniform, wherein each post is coated with a ligand, and wherein the pitch between adjacent posts each post set is less than about 100 nm; the regions comprising a gradient of pitch values designed for measuring the spatial dependence of binding of one analyte molecule to a ligand-coated post set, wherein the pitch is the distance between center points of adjacent posts in a post set and the gradient is a gradual change in the pitch values between the regions;

(b) contacting the surface of the device with a fluid sample; and (c) determining whether or not one analyte in the fluid sample simultaneously interacts or binds to a set of the ligand-coated posts in a region, thereby identifying the presence of the analyte in the fluid sample.

4. The method of claim 3, further comprising the step of purifying the analyte.

5. The method of claim 3, wherein the gradient of pitch values comprises from about 5 nm to about 100 nm.

6. A kit for determining the presence or absence of an analyte in a sample or for determining a subject's risk for developing a disease or for monitoring the status of a disease in a subject which comprises a device comprising (a) a substrate having a surface; and (b) regions on the surface, each region comprising an ordered, two-dimensional array of post sets over the surface, where the pitch between adjacent posts of a post set within a region is uniform, wherein each post is coated with a ligand, and wherein the pitch between adjacent posts of a post set is less than about 100 nm; the regions comprising a gradient of pitch values designed for measuring the spatial dependence of binding of one analyte to a post set; wherein sets of the ligand-coated posts can specifically bind to an analyte in an amount effective for detection of an analyte in the sample; and wherein the pitch is the distance between center points of adjacent posts of a post set and the gradient is a gradual change in the pitch values from one region to another.

7. The kit of claim 6, wherein the sample comprises a blood sample or a serum sample.

8. The kit of claim 6, wherein the kit further comprises one or more reagents for detecting amounts of the one or more analytes bound to the device.

9. The kit of claim 6, wherein the analyte is labeled with a detectable marker.

10. A method for detecting a protein isomer in a mixture, the method comprising (a) providing a device comprising a substrate having a surface; the surface comprising regions, each region comprising an ordered, two-dimensional array of post sets over the surface, wherein each post is coated with a ligand, and wherein the pitch between adjacent posts in a post set within a region is uniform; the pitch between adjacent posts in a post set is less than about 100 nm; the regions comprising a gradient of pitch values designed for measuring the spatial dependence of binding of one analyte to a post set; and wherein the pitch is the distance between center points of adjacent posts in a post set and the gradient is a gradual change in the pitch values from one region to another;

(b) contacting the surface of the device with a mixture; and (c) determining whether or not a protein isomer in the mixture interacts or binds to ligand-coated post sets in a region, thereby detecting the protein isomer in the mixture.

11. The method of claim 10, comprising detecting exactly one protein isomer.

12. The method of claim 10, wherein the gradient of pitch values is about 5 nm to about 100 nm.

13. A method for detecting a microorganism in a fluid sample, the method comprising (a) providing a device comprising a substrate having a surface; the surface comprising regions, each region comprising an ordered, two-dimensional array of post sets over the surface, wherein each post is coated with a ligand, and wherein the pitch between adjacent posts in a post set within a region is uniform and is less than about 100 nm; the regions comprising a gradient of pitch values designed for measuring the spatial dependence of binding of one analyte to a post set; and wherein the pitch is the distance between center points of adjacent posts in a post set and the gradient is a gradual change in the pitch values from one region to another;

(b) contacting the surface of the device with a fluid sample; and (c) determining whether or not a microorganism in the fluid sample interacts or binds to ligand-coated post sets in a region, thereby detecting the microorganism in the fluid sample.

14. The method of claim 13, wherein the microorganism is *Bacillus anthraxis, Clostridium botulinum, Brucella*, encephalitis virus, Ebola virus, Marburg virus, plague, tularemia, or smallpox.

15. The method of claim 13, wherein the microorganism is *Bacillus* anthraxis.

16. The method of claim 13, wherein the gradient of pitch values comprises from about 5 nm to about 100 nm.

17. The device of claim 1, wherein the protein molecule further comprises DNA or RNA.

18. The method of claim 6, wherein the gradient of pitch values is from about 5 nm to about 100 nm.

* * * * *